(12) United States Patent
Mudd

(10) Patent No.: US 9,220,843 B2
(45) Date of Patent: *Dec. 29, 2015

(54) EXTENDABLE PLUNGER ROD FOR MEDICAL SYRINGE

(71) Applicant: Allergan, Inc., Irvine, CA (US)

(72) Inventor: Christopher S. Mudd, Ventura, CA (US)

(73) Assignee: Allergan, Inc., Irvine, CA (US)

( * ) Notice: Subject to any disclaimer, the term of this patent is extended or adjusted under 35 U.S.C. 154(b) by 32 days.

This patent is subject to a terminal disclaimer.

(21) Appl. No.: 13/969,302

(22) Filed: Aug. 16, 2013

(65) Prior Publication Data

US 2014/0058335 A1  Feb. 27, 2014

Related U.S. Application Data

(63) Continuation of application No. 12/944,102, filed on Nov. 11, 2010, now Pat. No. 8,535,278.

(60) Provisional application No. 61/303,372, filed on Feb. 11, 2010.

(51) Int. Cl.
   A61M 5/315  (2006.01)

(52) U.S. Cl.
   CPC ....... *A61M 5/31511* (2013.01); *A61M 5/31505* (2013.01); *A61M 2005/31518* (2013.01)

(58) Field of Classification Search
   CPC ............... A61M 5/31505; A61M 5/31511; A61M 2005/31518
   USPC ................... 604/311, 218, 219, 42
   See application file for complete search history.

(56) References Cited

U.S. PATENT DOCUMENTS

| | | | | |
|---|---|---|---|---|
| 3,243,837 A | * | 4/1966 | Smith | ............................ 16/429 |
| 4,583,973 A | * | 4/1986 | Humphrey et al. | ........... 604/135 |
| 2006/0178641 A1 | | 8/2006 | Reynolds | |

* cited by examiner

*Primary Examiner* — Edelmira Bosques
(74) *Attorney, Agent, or Firm* — Linda Allyson Nassif

(57) ABSTRACT

A medical syringe with an extendible plunger rod is provided which facilitates injection of a large volume of material, for example, a dermal filler. The rod may include an outer plunger rod, an inner plunger rod, a compression spring configured to exert force tending to push the inner plunger rod in a direction distal to the outer plunger rod, and a locking mechanism. The locking mechanism prevents movement of the inner plunger rod relative to the outer plunger rod while both the inner and outer plunger rods are depressed, until the outer plunger rod has been depressed a first predetermined distance.

6 Claims, 7 Drawing Sheets

EXTENDABLE PLUNGER ROD FOR MEDICAL SYRINGE

RELATED APPLICATION

This application is a continuation of U.S. patent application Ser. No. 12/944,102, filed Nov. 11, 2010, which claims the benefit of, and priority to, U.S. Provisional Patent Application No. 61/303,372, filed on Feb. 11, 2010, the entire disclosure of which is incorporated herein by this reference.

BACKGROUND

A number of medical applications require the injection of significant amounts of material. For example, one such application is the injection of dermal fillers to correct facial wrinkles or folds. In such a procedure, a possibly significant quantity of dermal filler material is injected under the skin using a syringe. In addition, the material injected may have a higher viscosity than the substances typically injected by syringe. For example, some dermal fillers may include gels, such as a gel made of hyaluronic acid. Traditional syringes and the plunger rods used with such syringes present a number of problems when used for such applications. For instance, in order to accommodate significant volumes of material, such syringes must typically have either a large length or cross-sectional area. Syringes with larger cross-sectional areas are often not practical, however, because the extrusion force required to operate a syringe increases with the cross-sectional area, this may be particularly problematic when injecting viscous fluids. Increasing the length of a traditional syringe, however, may significantly increase the overall length of the device, as a longer plunger may also need to be used, which may reduce the user's comfort and control during use. Accordingly, example embodiments provide improved plunger rods which may address a number of the shortcomings of traditional plunger rods.

SUMMARY

Some example embodiments may provide an extendable plunger rod for use with a syringe having a syringe body, which may include an outer plunger rod with a proximal end and a distal end, the outer plunger rod having an inner cavity; an inner plunger rod, housed at least partially within the inner cavity of the outer plunger rod; a compression spring disposed within the inner cavity of the outer plunger rod and between the proximal end of the outer plunger rod, and the inner plunger rod, the compression spring configured to exert force tending to push the inner plunger rod in a direction distal to the outer plunger rod; and a locking mechanism, the locking mechanism configured to prevent movement of the inner plunger rod relative to the outer plunger rod while both the inner and outer plunger rods are depressed into a syringe body, until the outer plunger rod has been depressed at least a first predetermined distance into the syringe body.

In some example embodiments the locking mechanism may include a locking ring encircling the inner plunger rod and the outer plunger rod at the distal end of the outer plunger rod, and, in example embodiments, the locking ring may be press-fit, adhered, bonded, or otherwise secured, for example, temporarily or removably secured, to the outer plunger rod.

Some example embodiments may also include a retention mechanism which may be configured to prevent movement of the inner plunger rod relative to the outer plunger rod, after the inner plunger rod has been extended a second predetermined distance out of the outer plunger rod. In example embodiments the retention mechanism may include a first retention rod disposed within a retention aperture formed in the inner plunger rod; and a first retention slot formed in the outer plunger rod and positioned to engage the first retention rod when the inner plunger rod is extended the second predetermined distance. Example embodiments may also include a retention spring disposed within the retention aperture and positioned to exert force tending to push the first retention rod out of the retention aperture, when the inner plunger rod is extended out of the outer plunger rod the second predetermined distance and the retention rod is aligned with the retention slot. In addition, some example embodiments may also include a second retention rod disposed within the retention aperture; and a second retention slot formed in the outer plunger rod opposite the first retention slot; where the retention aperture passes through the inner plunger rod; and where the retention spring is positioned between the first and second retention rods to push the first and second retention rods apart and out of the retention aperture.

In some example embodiments, the locking mechanism may be configured to disengage when the outer plunger rod moves the first predetermined distance into the syringe body.

In other example embodiments the locking ring may be configured to be pressed off the outer plunger rod by contact with the syringe body.

In still other example embodiments the compression spring may be in a compressed state when the locking mechanism is engaged.

In some example embodiments the retention aperture may be positioned such that the retention aperture is inside the syringe body when the locking mechanism is disengaged.

Some example embodiments may also include an alignment rib formed on the inner plunger rod; and an alignment slot formed in the outer plunger rod; where the alignment rib may be shaped to slide within the alignment slot; and where the alignment rib and the alignment slot may be positioned such that the first retention rod slides into position to engage the first retention slot when the inner plunger rod is extended the second predetermined distance. In some example embodiments the alignment rib may extend less than an entire length of the inner plunger rod. In other example embodiments the alignment rib may extend an entire length of the inner plunger rod. And in some example embodiments the alignment rib may be located on a cap affixed to a proximal end of the inner plunger rod.

Some example embodiments may also include an alignment rib formed on the outer plunger rod; and an alignment slot formed in the inner plunger rod; where the alignment rib may be shaped to slide within the alignment slot; and where the alignment rib and the alignment slot may be positioned such that the first retention rod slides into position to engage the first retention slot when the inner plunger rod is extended the second predetermined distance.

In some example embodiments, the compression spring may be configured to provide sufficient force to extend the inner plunger rod from a retracted position, where the locking mechanism is engaged, to an extended position, where the retention mechanism engages.

Other example embodiments may provide a syringe device, which may include a syringe body; and any of the extensible plunger rods disclosed herein.

Yet other example embodiments may provide a method of using an extendable plunger rod with a syringe, the plunger rod having an inner plunger rod and outer plunger rod, the inner plunger rod disposed within the outer plunger rod, which may include applying pressure to the plunger rod, pushing the plunger rod into the syringe, until a locking mechanism, preventing the inner plunger rod from sliding relative to the outer plunger rod, is disengaged; releasing the applied pressure, allowing the inner plunger rod to extend out of the outer plunger rod a predetermined distance; and applying pressure to the plunger rod until a proximal end of the plunger rod has reached a proximal end of the syringe.

Still other example embodiments may provide an extendable plunger rod for use with a syringe having a syringe body, which may include an outer plunger rod with a proximal end and a distal end, the outer plunger rod having an inner cavity; an inner plunger rod, housed at least partially within the inner cavity of the outer plunger rod; a compression spring disposed within the inner cavity of the outer plunger rod and between the proximal end of the outer plunger rod, and the inner plunger rod, the compression spring configured to exert force tending to push the inner plunger rod in a direction distal to the outer plunger rod; a locking ring, the locking ring encircling the inner plunger rod and the outer plunger rod at the distal end of the outer plunger rod, the locking ring preventing movement of the inner plunger rod relative to the outer plunger rod while both the inner and outer plunger rods are depressed into a syringe body, until the outer plunger rod has been depressed at least a first predetermined distance into the syringe body; a first and second retention rod disposed within a retention aperture passing through the inner plunger rod; a first and second retention slot formed in the outer plunger rod, the first retention slot opposite the second retention slot; a retention spring positioned between the first and second retention rods and configured to push the first and second retention rods apart and out of the retention aperture, when the first and second retention rods are aligned with the first and second retention slots; an alignment slot formed in the outer plunger rod; and an alignment rib, shaped to slide within the alignment slot, formed on the inner plunger rod; where the alignment rib and the alignment slot may be positioned such that the first and second retention rods slide into position to engage the first and second retention slots when the inner plunger rod is extended out of the outer plunger rod a second predetermined distance.

BRIEF DESCRIPTION OF THE DRAWINGS

The present invention will be more readily understood from a detailed description of example embodiments taken in conjunction with the following figures.

DETAILED DESCRIPTION

Figure 1:
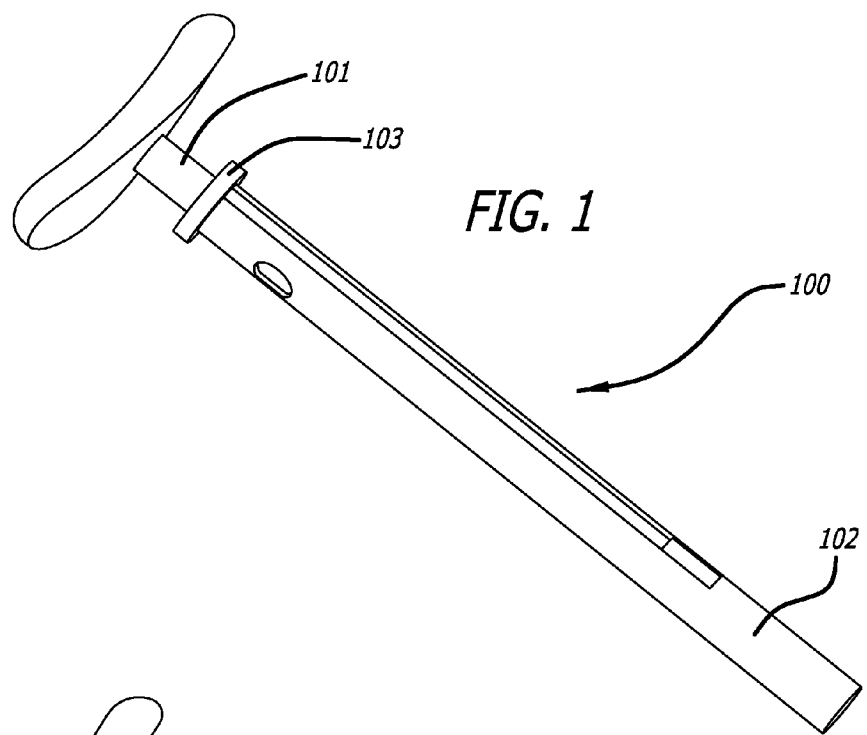
FIG. 1 illustrates an example extendable plunger rod in accordance with an example embodiment.

As discussed above, in many procedures a large fluid injection volume is needed. This usually requires increasing the syringe's length and/or its inner diameter, to accommodate a greater volume of material. Increasing the length of the syringe is typically not practical with a standard medical syringe, however, because the length of the plunger rod also has to be lengthened, which results in a longer maximum finger span needed to operate the syringe. Here, finger span refers to the distance between a user's thumb (which is positioned on the thumb grip of the plunger rod during use), and the fore finger and middle finger (which are positioned on the finger grip of the syringe). When the finger span needed to use the syringe becomes too large, it may become uncomfortable, difficult, or impossible for a user to operate the syringe, and may also result in diminished ability to perform a controlled injection. Thus there are practical limits on syringe length. Increasing the syringe's inner diameter, therefore, is one of the most common solutions for increasing the injection volume. When the inner diameter is increased, however, the syringe's cross-sectional area is correspondingly increased, which results in a higher extrusion force. This is particularly problematic when injecting high viscosity fluids or gels, as it makes it very difficult for the user to exert enough force for extrusion.

Example embodiments may resolve these problems by, for example, providing extendable plunger rods, which may be suitable for use with a syringe, for example a standard medical syringe. For instance, some example embodiments provide a single-use, extendable plunger rod which may be used along with a standard medical syringe for the injection of injectable substances, for example low to high viscosity liquids or gels.

Such example embodiments may allow for the injection of a larger volume of material, comfortably and easily. For instance, by providing an extendable plunger rod some example embodiments allow for a decrease in the finger span required to use a standard medical syringe, without altering the size or width of the syringe. As noted, decreasing this distance increases both the comfort and the control a user experiences while using the modified plunger and syringe. In addition, example embodiments may allow for the use of a shorter overall syringe length (including plunger rod), as compared to an equivalent volume standard medical syringe, which may allow a user's hands to get closer to the area of injection, providing more control during injection. Example embodiments may also allow for the use of the syringes which can accommodate a larger injection volume without increasing the inner diameter of the syringe, thus keeping the injection force low, while not increasing the finger span needed to operate the device. Such example embodiments allows the user to inject fluid or gel out of a longer syringe barrel without increasing the extrusion force, while maintaining a comfortable finger span.

FIG. 1, for example, illustrates an extendable plunger rod 100 in accordance with an example embodiment. As illustrated in FIG. 1, the plunger rod 100 may include an inner plunger rod 101 and an outer plunger rod 102. As seen in the illustration, the outer plunger rod 102 and the inner plunger rod 101 may both be shaped substantially in the form of a shaft or tube. In addition, the outer plunger rod 102 may be larger than the inner plunger rod 101 and may have a bore running a portion of its length, such that the inner plunger rod 101 may be fully or partially disposed within the body of the outer plunger rod 102. Also, as illustrated in FIG. 1, example embodiments may include a locking ring 103, which may be disposed around the inner plunger rod 101 and on or near the end of the outer plunger rod 102. Such a locking ring 103 may be designed to lock the inner plunger rod 101 in place, such that it may not move relative to the outer plunger rod 102 until the locking ring 103 is released, as is described in more detail below. It is noted that, in other example embodiments, other locking mechanisms may be used.

Figure 9:
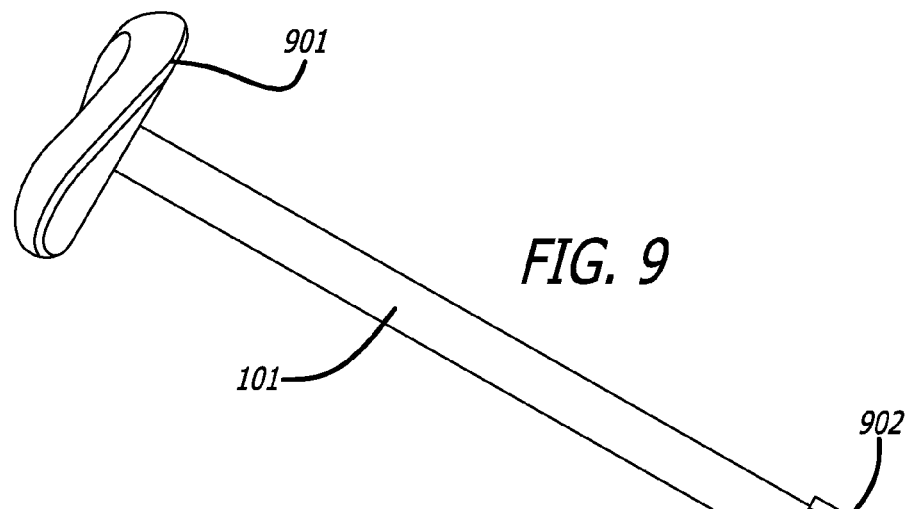
FIG. 9 illustrates an example inner plunger rod in accordance with an example embodiment.

An example inner plunger rod 101 may be seen in more detail in FIG. 9. As noted, the body of the inner plunger rod 101 may be substantially in the form of a shaft or tube. The inner plunger rod 101 need not have a round cross section. Rather, the inner plunger rod 101 may have any reasonable shape. In addition, the inner plunger rod 101 may be manufactured from common materials used for a typical plunger rod that is used with a single-use or multi-use syringe, for example metals, thermoplastics, thermoplastic elastomers (TPEs), silicones, glass, and the like, or may be manufactured from any combination of materials.

In addition, the inner plunger rod 101 may include a number of other structures. For instance, one end of the inner plunger rod 101, distal from the point of injection during use, may be attached to a thumb grip 901 (the terms proximal and distal, as used herein, are to be understood in relation to the point of injection during use). Such a thumb grip 901 may have the same function and similar design as the thumb grips used on typical plunger rods. The grip 901 may allow a user to apply pressure to the inner plunger rod 101, in order to push the plunger rod 100 into a syringe.

Example inner plunger rods 101 may also include an alignment rib 902. The alignment rib 902 may serve to properly align the inner plunger rod 101 with the outer plunger rod 102. Such an alignment rib 902 may take any shape or size. For example the alignment rib 902 may be shaped as a tab extending radially outward from the inner plunger rod 101, and shaped to fit and slide within a groove formed in the outer plunger rod 102. Multiple alignment ribs 902 may be provided which may be made out of the same material as the inner plunger rod 101, or made from a different material. Also, it is noted that, in other example embodiments, the alignment rib 902 may be attached to, or may be part, of the outer plunger rod 102 instead. In such embodiments an alignment groove or track may be provided on the inner plunger rod 101.

Example inner plunger rods 101 may also include a retention hole 903. As will be described more fully below, the retention hole 903 may house a retention assembly, which may be designed to engage when the plunger rod 100 is in it fully extended position, locking the position of the inner 101 and outer 102 plunger rods relative to each other. The retention hole 903 may be of any size or shape suitable for housing the retention assembly and may pass entirely through the inner plunger rod 101 or may provide a recess in the inner plunger rod 101. In addition, more than one retention hole 903 may be provided. Also, the retention hole 903 may be formed directly in the inner plunger rod 101, or may be formed in a piece that attaches to the inner plunger rod 101, for instance, a cap assembly which may attached to the end of the inner plunger rod 101. In some examples, a cap assembly may be used which may include both a retention hole 903 and an alignment rib 902. It is noted that, in other example embodiments, other locking mechanisms may be employed which may or may not include the use of a retention hole 903, e.g., tab, ridges, etc.

Figure 10:
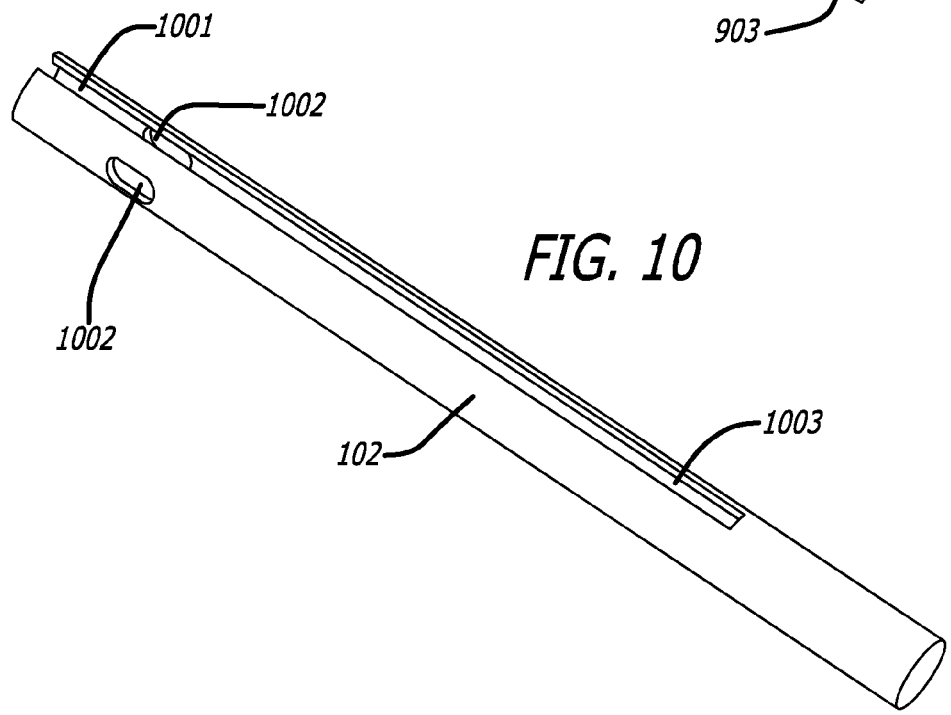
FIG. 10 illustrates an example outer plunger rod in accordance with an example embodiment.

An example outer plunger rod 102 is illustrated in FIG. 10. Like the inner plunger rod 101, the outer plunger rod 102 may have substantially the shape of a shaft or tube. Again, the outer plunger rod 102 may be manufactured from common materials used for a typical plunger rod that is used with a single-use or multi-use syringe, including, e.g., metals, thermoplastics, thermoplastic elastomers (TPEs), silicones, glass, or any combination thereof.

In addition, the outer plunger rod 102 may include a number of features. First, the outer plunger rod 102 may have an inner diameter 1001. For example, the outer plunger rod 102 may have a bore extending through all or a portion of the length of the tube. The inner diameter 1001 may be sufficiently large and of a shape that the inner plunger rod 101 may slide securely but freely into and within the inner diameter 1001. The bore that forms the inner diameter 1001 may be of any length, and may be, for example, of a length capable of housing a portion of the inner plunger rod 101 and a compression spring when in a retracted state.

The outer plunger rod 102 may also have a retention slot 1002. Multiple retention slots 1002 may be provided, which may be of any shape or size. For example, as depicted in FIG. 10, two retention slots 1002 may pass through the body of the outer plunger rod 102 opposite each other. Alternatively the slot 1002 may be a recess formed in the inner diameter 1001 of the outer plunger rod 102, but may not pass entirely through the body of the outer plunger rod 102. The retention slot 1002 may be positioned such that it is able to engage with a retention assembly housed in the retention hole 903 of the inner plunger rod 101, when the plunger rod 100 is extended. As noted above, in other example embodiments, a locking mechanism may be provided which does may or may not include the use of retention slots 1002, e.g., using tabs, ridges, etc.

In addition, the outer plunger rod 102 may also include an alignment slot 1003. The alignment slot 1003 may serve to properly align the inner plunger rod 101 with the outer plunger rod 102 in order to ensure that a retention assembly housed in the retention hole 903 will be aligned to properly deploy inside the retention slots 1002, when the plunger rod 100 is extended. There can be any number of alignment slots 1003, one slot is illustrated in the example, of any length and/or width, which may or may not extend the entire length of the outer plunger rod 102. As depicted, the alignment slot 1003 may pass entirely through the body of the outer plunger rod 102, between the outside of the rod 102 and the inner diameter 1001. In other examples, the alignment slot 1003 may not pass through the body of the outer plunger rod 102 but, rather, may be a recess formed in the inner diameter 1001 of the outer plunger rod 102. In addition, the alignment slot 1003 may be sized and shaped to allow the alignment rib 902 of the inner plunger rod 101 to slide within it.

Figure 2:
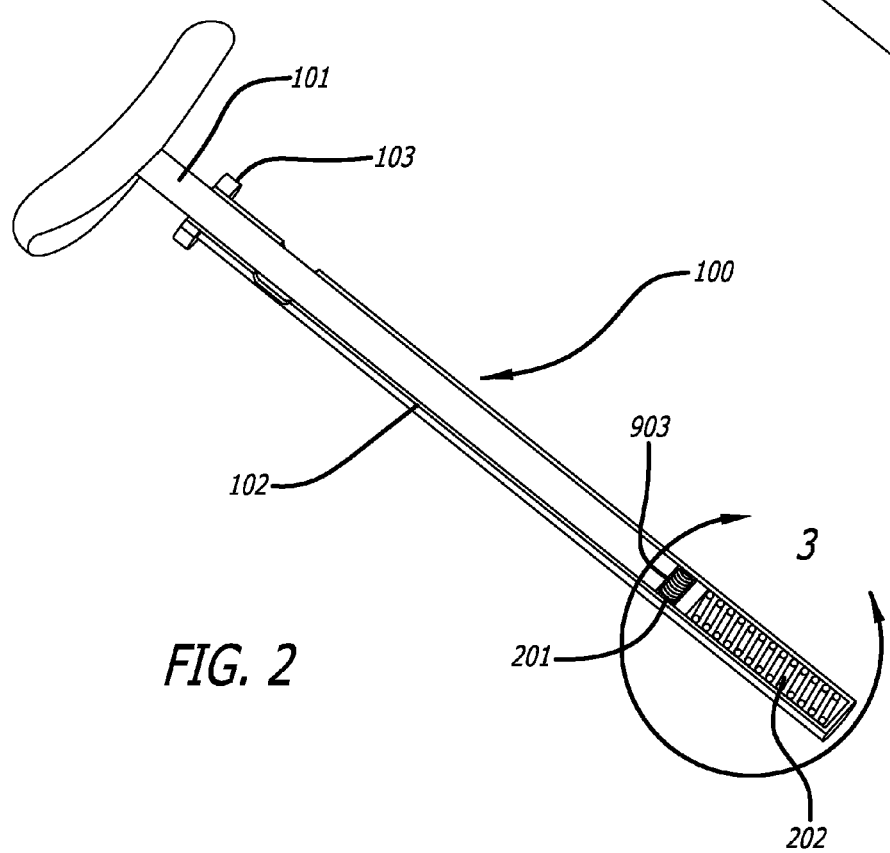
FIG. 2 illustrates a cross-section of an example extendable plunger rod in accordance with an example embodiment.

FIG. 2 illustrates a cross-sectional view of an example extendable plunger rod 100. In FIG. 2, the plunger rod 100 is in its retracted position. As illustrated, the inner plunger rod 101 extends into the outer plunger rod 102. In this retracted state, a greater length of the inner plunger rod 101 is housed within the outer plunger rod 102, than would be when the plunger rod 100 is extended. Also as shown in the figure, a retention assembly 201 is housed inside the retention hole 903 in the inner plunger rod 101. In addition, a compression spring 202 is located in the bore of the outer plunger rod 101, between a proximal end of the inner plunger rod 101 and a proximal end of the outer plunger rod 102. In this retraced position, the compression spring 202 is compressed.

FIG. 2 also illustrates that the locking ring 103 may be attached to the outer plunger rod 102, when the plunger rod 100 is in the retracted position. In the illustrated example, the locking ring 103 may be press-fitted around the outer plunger rod 102. In this state, the locking ring 103 may prevent the inner plunger rod 101 from sliding within the outer plunger rod 102. As such, the locking ring 103 may maintain the extendable plunger rod 100 in the retracted position and prevent the compression spring 202 from expanding. In other embodiments, the locking ring may be adhered, bonded, or otherwise secured, for example, temporarily or removably secured, to the outer plunger rod.

Figure 11:
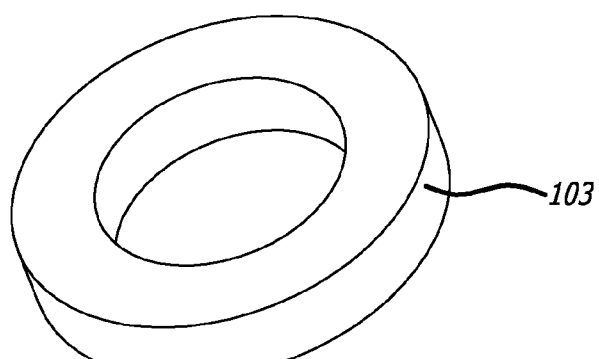
FIG. 11 illustrates an example locking ring in accordance with an example embodiment.

FIG. 11 illustrates a detailed drawing of an example locking ring 103. The locking ring's primary purpose is to hold the inner plunger rod 101 and outer plunger rod 102 together until the locking ring 103 is disengaged from the assembly. To this end, the locking ring 103 may be shaped so that it may fit around the inner plunger rod 101 and be press-fit onto the distal end of the outer plunger rod 102. Once disengaged, the inner plunger rod 101 may be able to freely move out of the outer plunger rod 102 a specific distance, with assistance from the compression spring 202. The locking ring 103 may be manufactured from any common materials, again including, for example, metals, thermoplastics, thermoplastic elastomers (TPEs), silicones, glass, or any combination thereof. In addition, the locking ring 103 may take any shape (e.g. round, oval, square, rectangular or polygon) and may be of any suitable size, for example having any suitable inner or outer diameter, width or length. In example embodiments, the locking ring may be shape such that it may be pressed off the outer plunger rod 102 on contact with the body of a syringe. In some examples, the locking ring 103 may also have additional features such as grooves, slots or cutouts.

Figure 3:
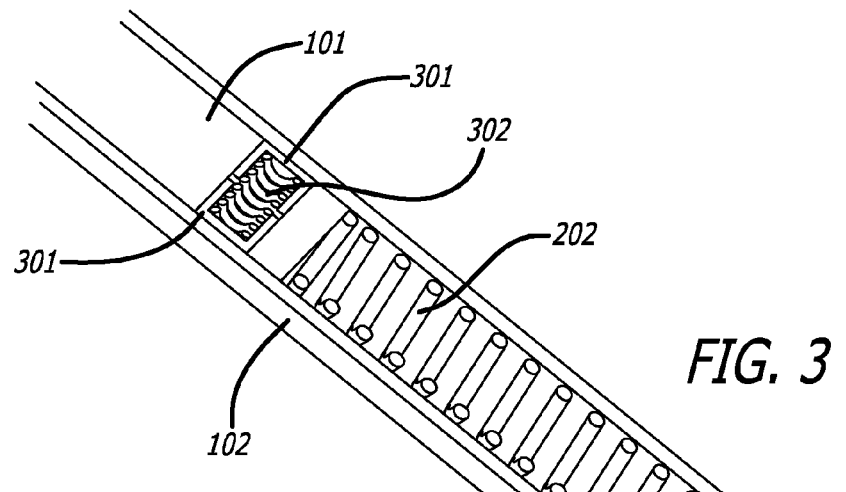
FIG. 3 illustrates a cross-section of an example extendable plunger rod in accordance with an example embodiment.

FIG. 3 illustrates a portion of the example plunger rod in its retracted state in a more detailed cross-section. Again, a portion of the inner plunger rod 101 may be seen within the outer plunger rod 102. As shown, the outer plunger rod 102 may be closed at the proximal end. The closer of the outer plunger rod 102 may be formed in any acceptable way. For example, the outer plunger rod 102 may be formed of a single piece, including the closed end. Alternatively, the outer plunger rod 102 may be formed in the shape of a tube which may then be fitted with a cap, which may, for example, be a plunger.

As noted, a compression spring 202 may be included within the outer plunger rod 102. The compression spring 202 may be located within the outer plunger rod 102, and may be capable of applying a force against the outer plunger rod 102 when compressed. For instance, as illustrated, a proximal end of the compression spring 202 may be placed against the proximal end of the outer plunger rod 102. The distal end of the spring 202 may rest against a proximal end of the inner plunger rod 101, such that, when the inner plunger rod 101 is moved into the outer plunger rod 102, the compression spring 202 may be compressed and may apply a force to both the inner 101 and outer 102 plunger rods, tending to push the inner plunger rod 101 away from the proximal end of the outer plunger rod 102 and, therefore, out of the outer plunger rod 102.

Figure 12:
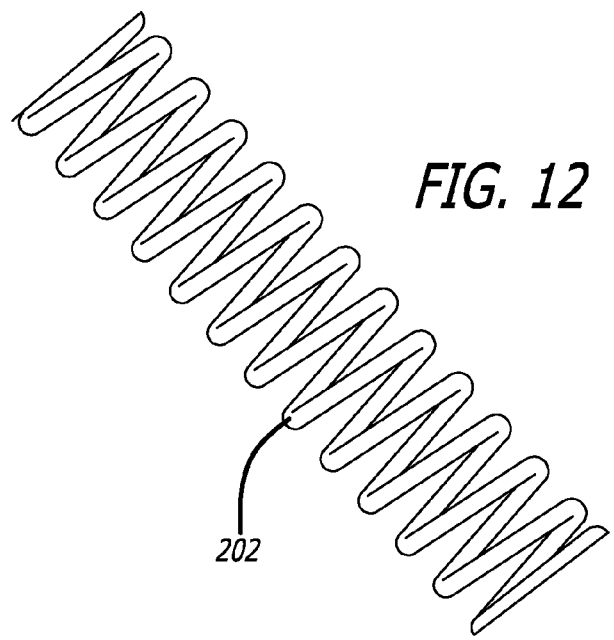
FIG. 12 illustrates an example compression spring in accordance with an example embodiment.

An example compression spring 202 is illustrated in detail in FIG. 12. The compression spring's 202 primary purpose is to extend the inner plunger rod 101 from the outer plunger rod 102 once the locking ring 103 is disengaged. The compression spring 202 may also be manufactured from any common materials, including, for example, metals, thermoplastics, thermoplastic elastomers (TPEs), silicones, or any combination thereof. It may also be any shape (e.g. round, oval, square, rectangular or polygon) or any size.

As explained, the compression spring may be designed to apply a force pushing the inner plunger rod 101 some length out of the outer plunger rod 102. Therefore, the compression spring should be shaped such that it is able to fit within the inner diameter 1001 of the outer plunger rod 102. In addition, it should be designed such that it is able to supply adequate force over the entire distance that the inner plunger rod 101 is designed to move.

It is noted that a physical spring need not actually be used. Rather, any system which may apply a force tending to push the inner plunger rod 101 away from the proximal end of the outer plunger rod 102, and thus out of the outer plunger rod 102, may be used. For instance, in some example embodiments, the space within the outer plunger rod 102, between the inner plunger rod 101 and the proximal end of the outer plunger rod 102, in which the compression spring 202 would be located, may be filled with a compressed gas which may apply a suitable force.

Returning to FIG. 3, the example plunger rod 100 may further include a retention assembly 201. The retention assembly 201 may be located within a retention hole 903 in the inner plunger rod 101, and may serve to lock the position of the inner plunger rod 101, relative to the outer plunger rod 102, when the plunger rod 100 is in its fully extended position, as further discussed below. As shown in the illustration, the retention assembly 201 may be made of two retention rods 301, which may be cup shaped as shown, or may have any other practical shape. Between the retention rods 301 may be a retention spring 302, which may be configured to apply a force tending to push the two retention rods 301 away from each other when compressed. As illustrated in FIG. 3, the retention assembly 201 is in its compressed state. As, shown, the ends of the retention rods 301 are pushed, by the retention spring 302, against the outer plunger rod 102, which does not allow them to move further. It is noted that any number of retention rods may be used, including only a single retention rod.

Figure 13:
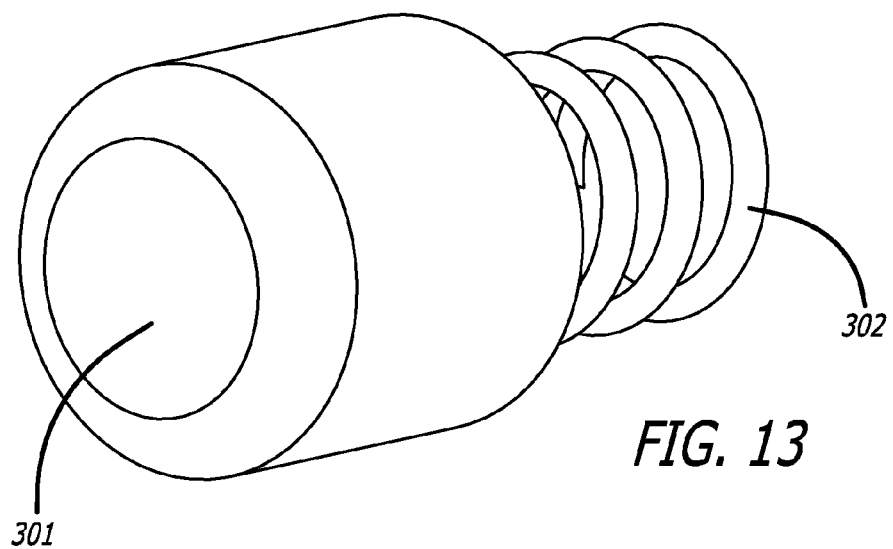
FIG. 13 illustrates an example retention rod in accordance with an example embodiment.

An example retention rod 301 and spring 302 are shown in FIG. 13. Retention rod's 301 primary purpose is to lock the inner plunger rod 101 and the outer plunger rod 102 together, such that they are unable to move relative to one another, once the inner plunger rod 101 has been extended by the compression spring 202. At such a point, the retention rods 301 may engage with the retention slots 1002 in the outer plunger rod 102. For example, once the inner plunger rod 101 has moved a sufficient distance, the retention rods 301 may slide into position over the retention slots 1002. As the retention rods 301 are no longer held back by the body of the outer plunger rod 102, the retention spring 302 may push the retention rods 301 outward into the retention slots 1002, locking the plunger rod 100 in its extended position. The retention rods 301 can be manufactured from any common materials, including, for example, metals, thermoplastics, thermoplastic elastomers (TPEs), silicones, or any combination thereof. It can be any shape (e.g. round, oval, square, rectangular or polygon) and any size. The retention rod 301 may be shaped and sized such that it is able to lock in the retention slot 1002 when positioned to engage with the slot 1002.

Figure 14:
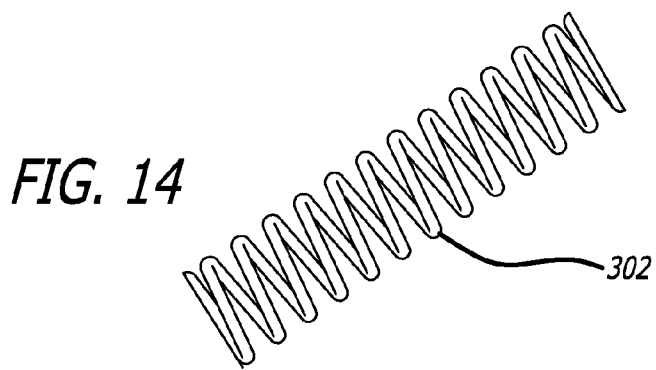
FIG. 14 illustrates an example retention spring in accordance with an example embodiment.
Figure 15A:
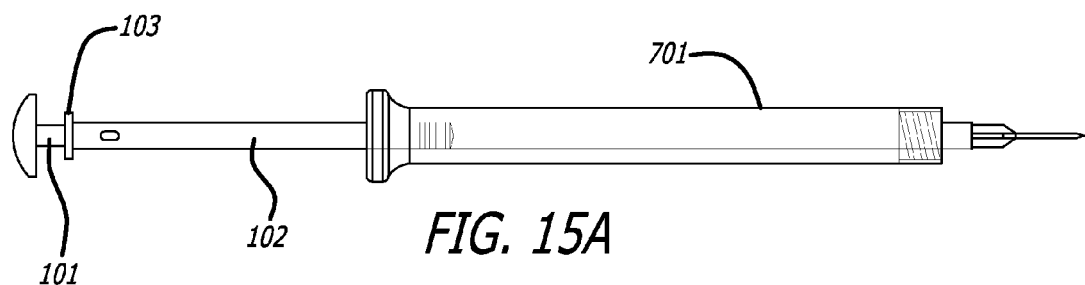
FIGS. 15A-15D illustrate an example extendable plunger rod in use with a syringe accordance with an example embodiment.
Figure 15B:
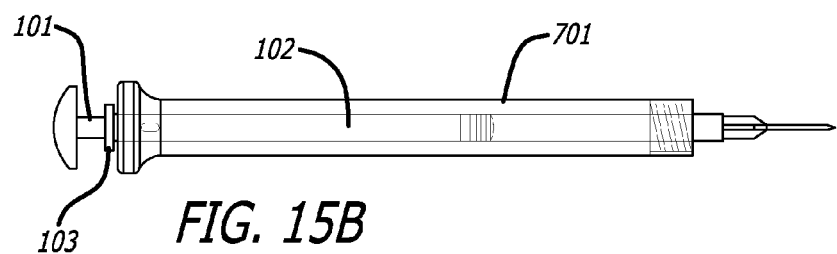
Figure 15C:
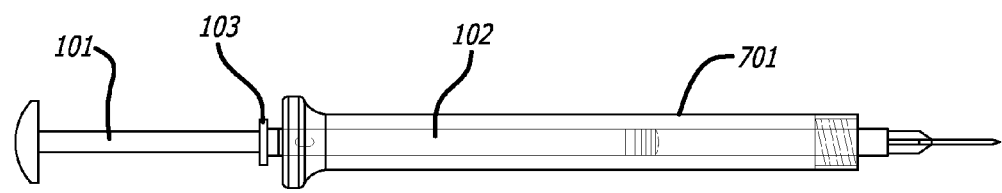
Figure 15D:
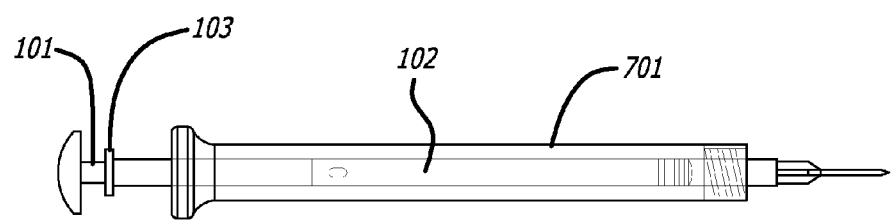

In example embodiments, the retention spring 302, shown in detail in FIG. 14, may be a compression spring whose primary purpose is to extend the retention rods 301 out of the inner plunger rod 101 once they have reached the retention slots 1002 of the outer plunger rod 102. The retention spring 302 can be manufactured from any common materials, including (but not limited to) metals, thermoplastics, thermoplastic elastomers (TPEs), silicones, or any combination thereof. It can be any shape (e.g. round, oval, square, rectangular or polygon) and any size.

Figure 4:
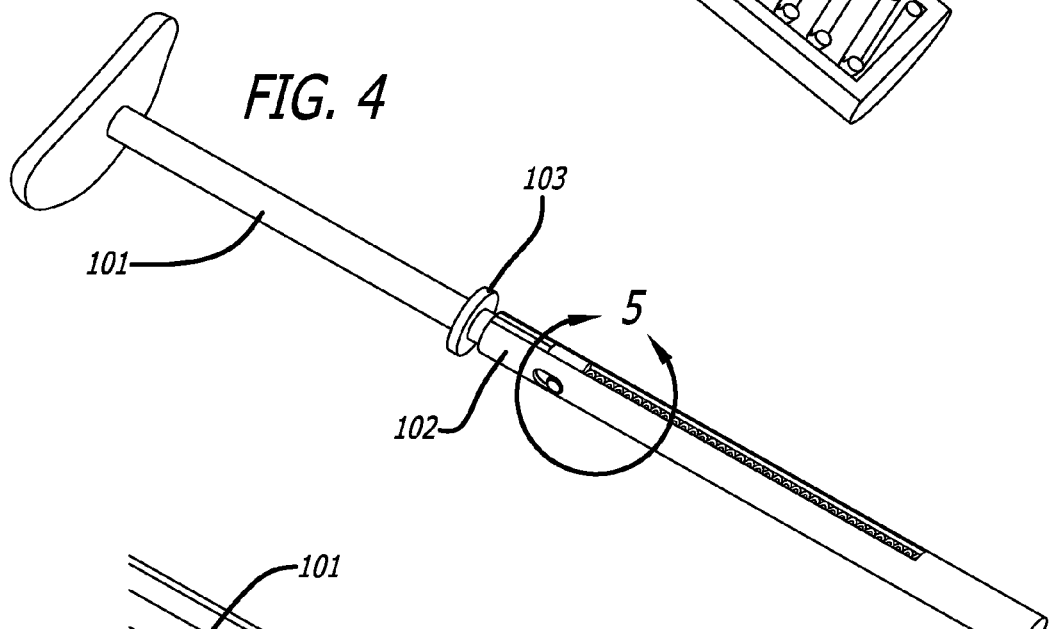
FIG. 4 illustrates an example extendable plunger rod in accordance with an example embodiment.

FIG. 4 depicts the example plunger rod 100 in its fully extended position. In this position, a portion of the inner plunger rod 101 has been extended out of its original location within the outer plunger rod 102. In this state, the overall length of the plunger rod 100 is longer than in its retracted state. Also shown in the figure, the locking ring 103 has been moved away from the outer plunger rod 102. As will be explained more fully below, in this position the locking ring 103 no longer fixes the position of the inner plunger rod 101 relative to the outer plunger rod 102, thus the force applied by the compression spring 202 was able to cause the rods 101, 102 to slide relative to one another into the extended position illustrated. As can be seen in the figure, the compression spring 202 in this extended state extends further along the length of the outer plunger rod 102, while a shorter length of the inner plunger rod 101 remains within the outer plunger rod 102.

Figure 5:
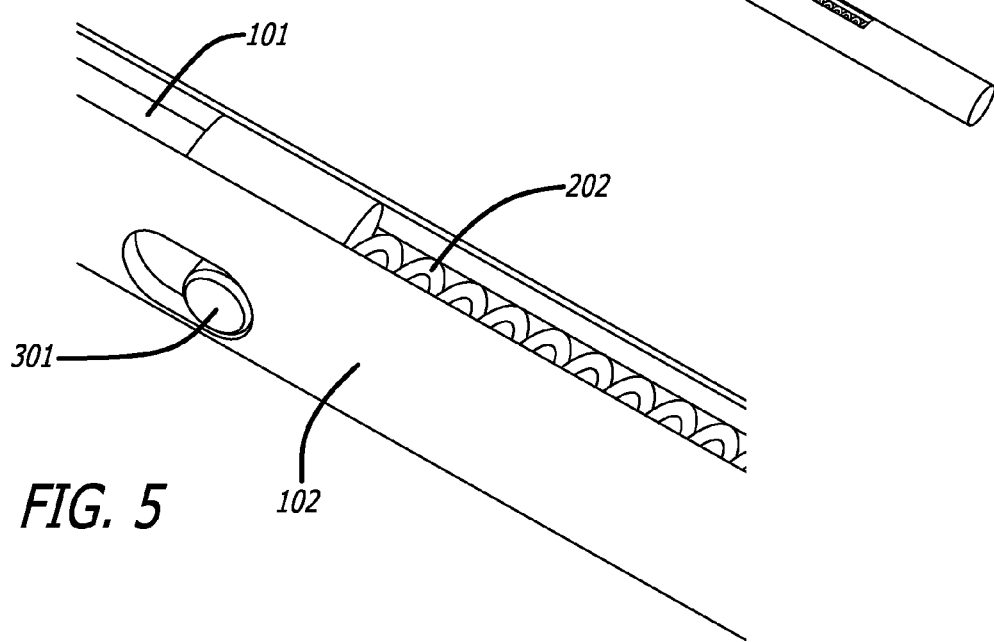
FIG. 5 illustrates an example extendable plunger rod in accordance with an example embodiment.

FIG. 5 shows an expanded detail of the example plunger rod 100 in its extended position. As shown in FIG. 5, the compression spring 202 has expanded, pushing the inner plunger rod 101 along and out of the outer plunger rod 102 some distance. Also as can be seen, the inner plunger rod 101 has moved far enough that the retention slots 1002 are positioned over the retention rods 301. Therefore, the retention spring 302 has expanded, pushing the retention rods 301 into the retention slots 1002. In this state, the retention rods 301 lock the plunger rod 100 in its extended position. It is noted here that, although not depicted, the portion of the plunger rod 100 containing the retention rods 301 may be within a syringe body at this point. Therefore, the retention rods 301 may not be able to extend beyond the depicted position as they are in contact with the syringe body.

Figure 6:
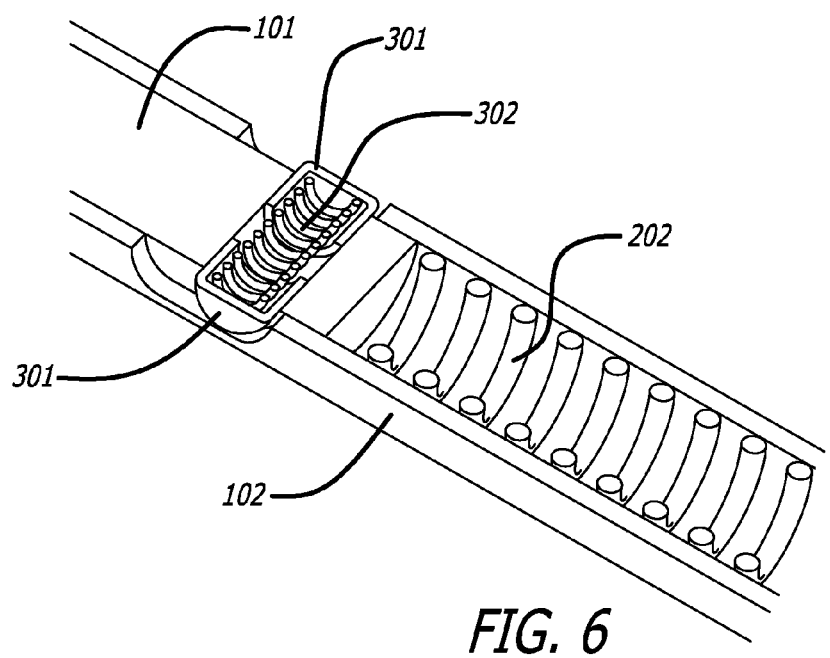
FIG. 6 illustrates a cross-section of an example extendable plunger rod in accordance with an example embodiment.

FIG. 6 illustrates a detailed cross-sectional view of a portion of the plunger rod 100 in extended form. As noted above, in the example embodiment illustrated, two retentions slots 1002, opposite each other, are located in the outer plunger rod 102. As can be seen in the cross-section, when the retention assembly 201 is positioned between the two retention slots 1002, the assembly 201 is able to expand into the slots 1002. In the example, the retention spring 302, which was compressed in the plunger rod's 100 retracted state, has pushed the two retention rods 301 apart, extending the retention assembly 201. Each retention rod 301, therefore, engages in its corresponding retention slot 1002, locking the position of the outer 102 and inner 101 plunger rods relative to each other.

Figure 7:
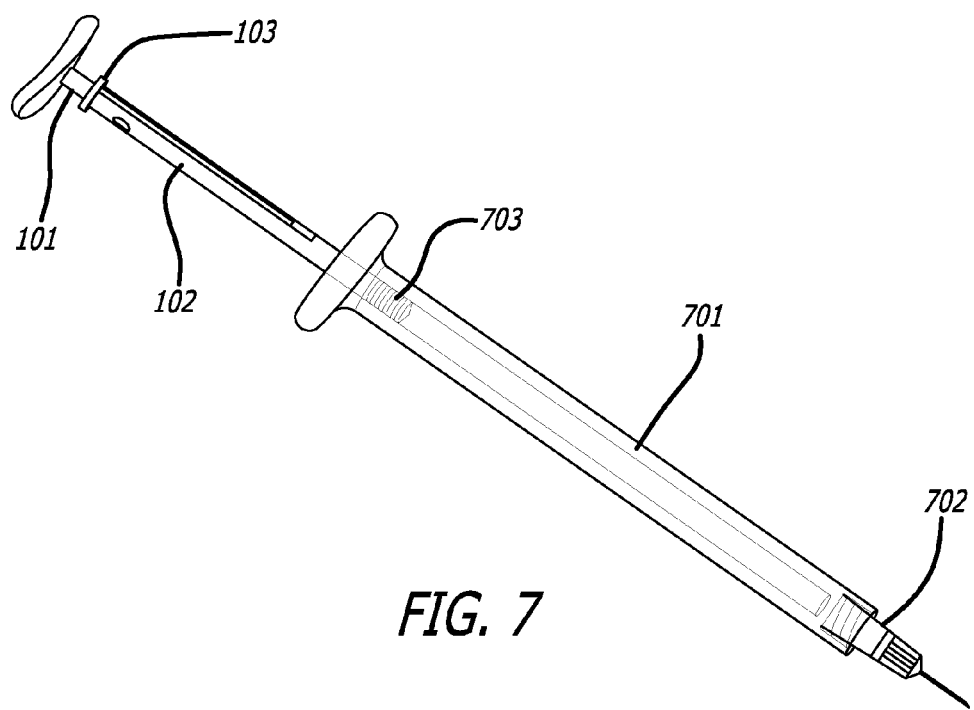
FIG. 7 illustrates an example extendable plunger rod with a syringe in accordance with an example embodiment.

FIG. 7 illustrates the example plunger rod 100 as it may be used with a syringe 701. The syringe 701 may be any kind of syringe used with a plunger. At a proximal end, the syringe 701 may be terminated with a needle 702, or other structure through which the contents of the syringe 701 are to be extruded. The syringe 701 may be shaped generally in the form of a tube and may have a hollow cavity, inside of which the material to be extruded may be located, when in use. Inserted into the distal end of the syringe 701 may be a plunger 703. The plunger 703 may be made of any materially typically used for such plungers and may be shaped so as to form a seal with the inner wall of the syringe 701. When pushed towards the proximal end of the syringe 701, the plunger 703 may slide within the syringe 701 and may force the material contained in the syringe 701 through the needle 702.

The plunger 703 itself may be in contact with the plunger rod 100, specifically the proximal end of the outer plunger rod 102, which may supply the force needed to move the plunger 703 through the syringe 701 and thus extrude the material. The plunger 703 may make contact with the plunger rod 100 in any reasonable manner. For instance, the plunger 703 may be connected to the plunger rod 100, for example affixed to the plunger rod 100 with an adhesive or in some other manner. The plunger 703 may be formed as in integral part of the plunger rod 100, or the plunger 703 may not be attached to the plunger rod 100 at all, but may simply be pushed by the plunger rod 100 in operation.

As illustrated in FIG. 7, the plunger rod 100 is initially in its retracted position. That is, the inner plunger rod 101 has been slid into the outer plunger rod 102 as far as it is capable of going. Thus the compression spring 202 is fully compressed, and the retention spring 302 is also compressed, and the retention rods 301 are not engaged in the retention slots 1002. In addition, locking ring 103 is in its locked position, preventing the compression spring 202 from extending the inner plunger rod 101.

Figure 8:
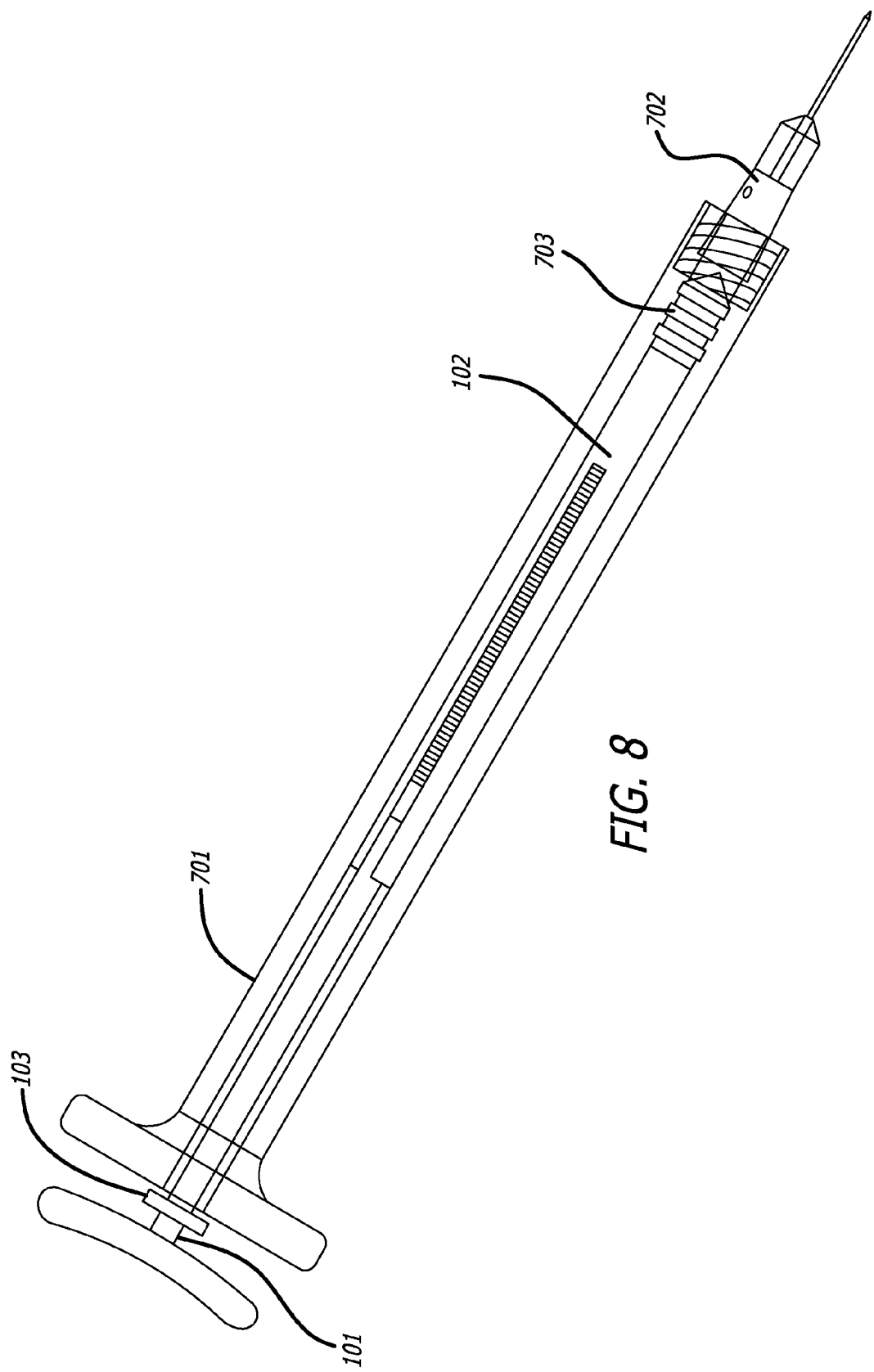
FIG. 8 illustrates an example extendable plunger rod with a syringe in accordance with an example embodiment.

FIG. 8 illustrates the example plunger rod 100 in its fully extended position inside the syringe 701. As seen in the drawing, the outer plunger rod 102 has been pushed into the syringe 701. In addition, the locking ring 103 has been removed from the outer plunger rod 102. Therefore, the locking ring 103 has released the inner 101 and outer 102 plunger rods, allowing them to slide relative to one another. Having done so, the compression spring 202 has pushed a length of the inner plunger rod 101, which was originally inside the outer plunger rod 102, out of the outer plunger rod 102. That length of the inner plunger rod 101 has now also been pushed into the syringe 701, causing the outer plunger rod 102 and the plunger 703 to move further towards the needle 702. Although not illustrated in this figure, as the plunger rod 100 is fully extended in this figure, the retention assembly 201 is engaged, locking the outer 102 and inner 101 rods in place.

The operation of an example plunger rod 100 may be illustrated with reference to FIG. 15. For example, the plunger rod 100 may be positioned in a syringe 701 of suitable size. When in the initial position 1501, the plunger rod 100 may be in its fully retracted position. The user may then hold the syringe 701 and push the plunger rod 100 as if a traditional medical syringe and plunger were being used. During this time, the locking ring 103 is in the locked position and is holding the inner plunger rod 101 inside the outer plunger rod 102 via, e.g., a press-fit. Also during this time, both the compression spring 202 and the retention spring 302 are in the compressed state and the retention rods 301 are in a retracted state.

The user may continue to exert force on the plunger rod 100, until the locking ring 103 makes contact with the end of the syringe 701, at position 1502, and is pressed off the outer plunger rod 102. At that point, the outer plunger rod 102 may have been extended entirely into the syringe 701. However, the plunger rod 100 may still have room to move forward. Thus, after the locking ring 103 is disengaged, the user may remove his/her thumb from the thumb grip 901 momentarily (e.g., less than 1 second).

During this moment (when pressure is not applied to the thumb grip 901, and thus the inner plunger rod 101), the compression spring 202 may uncompress and extend the inner plunger rod 101 to a specific position (where the retention rods 301 line up with the retention slots 1002 on the outer plunger rod 102). Once the retention rods 301 are aligned with the retention slots 1002, the retention spring 302 is able to uncompress and extend the retention rods 301 into the slots 1002. It is noted that, the retention rods 301 may not be fully ejected from the assembly, because they may be held to a maximum extension by the inner wall of the syringe 701 barrel. The retention rods 301 lock in the retention slots 1002 and prevent the inner plunger rod 101 from being pushed further out of the outer plunger rod 102 (or further into once pressure is reapplied to the plunger rod 100), thus fixing the plunger rod 100 in its extended state, as show in position 1503.

The user may then reapply pressure to the thumb grip 901. At this point the retention rods 301 may transfer that pressure to the outer plunger rod 102, allowing the user to press the plunger rod 100 until all material is extruded out of the syringe 703, at position 1504.

In the preceding specification, the present invention has been described with reference to specific example embodiments thereof. It will, however, be evident that various modifications and changes may be made thereunto without departing from the broader spirit and scope of the present invention. The description and drawings are accordingly to be regarded in an illustrative rather than restrictive sense.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A dermal filler syringe comprising:
   a syringe body; and
   an extendable plunger rod including
      an outer plunger rod with a proximal end and a distal end, the outer plunger rod having an inner cavity,
      an inner plunger rod, housed at least partially within the inner cavity of the outer plunger rod,
      a compression spring disposed within the inner cavity of the outer plunger rod and between the proximal end of the outer plunger rod, and the inner plunger rod, the compression spring configured to exert force tending to push the inner plunger rod in a direction distal to the outer plunger rod,
      a locking mechanism, the locking mechanism configured to prevent movement of the inner plunger rod relative to the outer plunger, the locking mechanism includes a locking ring encircling the inner plunger rod and the outer plunger rod at the distal end of the outer plunger rod, and
      a retention mechanism configured to prevent movement of the inner plunger rod relative to the outer plunger rod, the retention mechanism comprising a first retention rod disposed within a retention aperture formed in the inner plunger rod, and a first retention slot formed in the outer plunger rod and positioned to engage the first retention rod.

2. The syringe of claim 1, wherein:
   the locking ring is press-fit onto the outer plunger rod.

3. The syringe of claim 2, wherein the locking ring is configured to be pressed off the outer plunger rod by contact with the syringe body.

4. The syringe of claim 1, wherein the locking mechanism is configured to disengage when the outer plunger rod moves the first predetermined distance into the syringe body.

5. The syringe of claim 1, wherein:
   the compression spring is in a compressed state when the locking mechanism is engaged.

6. The syringe of claim 1, wherein:
the compression spring is configured to provide sufficient force to extend the inner plunger rod from a retracted position, where the locking mechanism is engaged, to an extended position, where the retention mechanism engages.

\* \* \* \* \*